United States Patent
Deitsch et al.

(10) Patent No.: US 7,805,320 B2
(45) Date of Patent: Sep. 28, 2010

(54) METHODS AND SYSTEMS FOR NAVIGATING A LARGE LONGITUDINAL DATASET USING A MINIATURE REPRESENTATION IN A FLOWSHEET

(75) Inventors: Andrew Isaac Deitsch, Lake In The Hills, IL (US); Christopher Scott Puryear, Schaumburg, IL (US); James Edward Jay, Volo, IL (US); Jyothi S. Jayaraman, Hoffman Estates, IL (US)

(73) Assignee: General Electric Company, Schenectady, NY (US)

( * ) Notice: Subject to any disclaimer, the term of this patent is extended or adjusted under 35 U.S.C. 154(b) by 311 days.

(21) Appl. No.: 11/972,050

(22) Filed: Jan. 10, 2008

(65) Prior Publication Data

US 2009/0183095 A1 Jul. 16, 2009

(51) Int. Cl.
*A61B 5/00* (2006.01)
*G06F 19/00* (2006.01)
(52) U.S. Cl. .............................................. 705/3; 705/2
(58) Field of Classification Search ................. 705/2–3; 600/345; 715/764
See application file for complete search history.

(56) References Cited

U.S. PATENT DOCUMENTS

| | | | |
|---|---|---|---|
| 7,260,547 B2 * | 8/2007 | Kameda | 705/3 |
| 7,383,071 B1 * | 6/2008 | Russell et al. | 600/345 |
| 2009/0150177 A1 * | 6/2009 | Buck et al. | 705/2 |
| 2009/0150812 A1 * | 6/2009 | Baker et al. | 715/764 |
| 2009/0222286 A1 * | 9/2009 | Elsholz | 705/3 |

OTHER PUBLICATIONS

General Electric Company—Google Finance, http://Finance.google.com/finance?q=ge&hl=en (2 pages).

* cited by examiner

*Primary Examiner*—Luke Gilligan
(74) *Attorney, Agent, or Firm*—Hanley, Flight & Zimmerman, LLC

(57) ABSTRACT

Certain embodiments of the present invention provide methods and systems for presentation of patient data via a flowsheet including a graphical map representation of the data and a timeline axis for data navigation. Certain embodiments provide a system including a flowsheet including a patient data set represented as a map with a timeline axis for the map, wherein the map is navigated to display data collected along the timeline, and an interface for accessing the flowsheet. Certain embodiments provide a method including displaying data for a patient via a flowsheet along with a timeline of events relating to the patient, wherein the data is represented in alphanumeric as well as graphical map form; navigating the patient data using the timeline; allowing a user to flag events in the patient data along the timeline; and defining a time period for presentation of patient data along the timeline in the flowsheet.

10 Claims, 3 Drawing Sheets

METHODS AND SYSTEMS FOR NAVIGATING A LARGE LONGITUDINAL DATASET USING A MINIATURE REPRESENTATION IN A FLOWSHEET

BACKGROUND OF THE INVENTION

The present invention generally relates to patient data aggregation and review. More particularly, the present invention relates to methods and systems providing a flowsheet including a miniature representation of a patient dataset with a navigation timeline.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, equipment and computerized information systems. Personnel in a healthcare facility must manage a plurality of patients, systems, and tasks to provide quality service to patients. Healthcare personnel may encounter many difficulties or obstacles in their workflow.

Healthcare practice has become centered around electronic data and records management. Healthcare environments, such as hospitals or clinics, include information systems, such as healthcare information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information for a particular information system may be centrally stored or divided at a plurality of locations. Healthcare practitioners may desire to access patient information or other information at various points in a healthcare workflow. For example, during an imaging scan of a patient, medical personnel may access patient information, such as a patient exam order, that are stored in a medical information system. Alternatively, medical personnel may enter new information, such as history, diagnostic, and/or treatment information, into a medical information system during an imaging scan.

Currently, relevant patient information for a patient's entire lifetime exists in a number of formats that include paper, folders and disparate information systems from a variety of vendors and a variety of healthcare providers. Current systems cannot aggregate this information effectively. Additionally, current systems cannot display this information at one time so that healthcare providers have the ability to interpret a patient's complete medical history when assessing and diagnosing illnesses. Providers are rarely able to see the full history of a patient. More commonly, providers have only the information that they have gathered or that they have received in response to questions asked of the patient in a clinical setting. Key decisions are made with the limited knowledge available to the provider at the point at which the provider is making a decision.

BRIEF SUMMARY OF THE INVENTION

Certain embodiments of the present invention provide methods and systems for presentation of patient data via a flowsheet including a graphical map representation of the data and a timeline axis for navigating the data.

Certain embodiments provide a healthcare information system providing a clinical flowsheet for data review. The system includes a clinical flowsheet including a patient healthcare data set represented as a map including a timeline as an axis for the map, wherein the map is navigated to display data collected at a certain part of the timeline. The system also includes an interface for accessing the flowsheet.

Certain embodiments provide a method for navigating a patient healthcare data set using a representation of the dataset in a flowsheet. The method includes displaying data for a patient via a flowsheet along with a timeline of events relating to the patient, wherein the data is represented in alphanumeric as well as graphical map form. The method also includes navigating the patient data using the timeline. The method further includes allowing a user to flag events in the patient data along the timeline. Additionally, the method includes defining a time period for presentation of patient data along the timeline in the flowsheet.

Certain embodiments provide a computer readable medium having a set of instructions for execution on a computer. The set of instructions includes a user interface routine displaying data for a patient via a flowsheet along with a timeline of events relating to the patient, wherein the data is represented in alphanumeric and graphical map form. The user interface routine facilitates navigation of the patient data using the timeline and allows a user to flag events in the patient data along the timeline. The set of instructions also includes a processing routine defining a time period for presentation of patient data along the timeline in the flowsheet.

Figure 1:
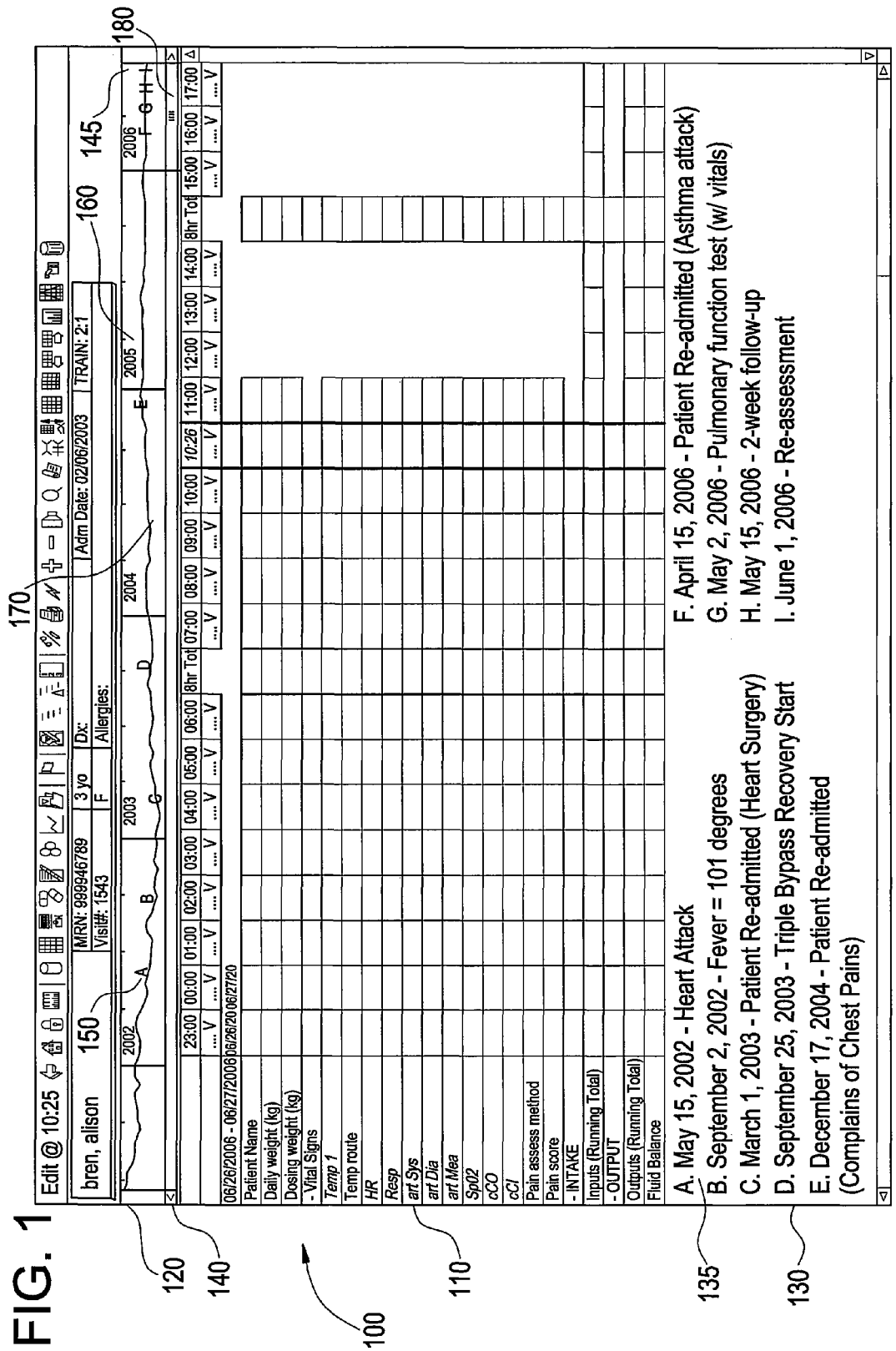
FIG. 1 illustrates a flowsheet used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Healthcare providers are frequently mobile and attending to multiple patients. Certain embodiments provide quicker and easier access to the patient data in a healthcare setting. Certain embodiments provide systems and methods that allow healthcare providers to locate a subset of available patient data and help facilitate a safe and effective clinical environment.

A flowsheet is a tool for tracking periodically assessed data, such as patient data. A sampling period can be changed so that the data is collected more or less frequently. The collected data can grow substantially over a period of time depending on the patient's length of stay, number of visits, the sampling period, etc. Healthcare providers may need or wish to look at the previous assessed data before they make any decisions on a patient care plan, for example.

Current flowsheet systems allow user(s) to navigate one day at a time or pick any subsequent day to look at the data. There is no easy way to quickly look at the data for a period without having to know the date and time, which could be a hindrance to the healthcare providers. Additionally, healthcare providers are often moving around and attending to multiple patients, further adding to complications when identifying and navigating through available data.

Certain embodiments provide a timeline navigation of the data collected over a period of time in a flowsheet. The dataset collected is represented as a miniature map including a timeline as a horizontal axis. Healthcare providers can navigate this map, which may display data collected at a certain period of time. Providers can quickly visualize variation of a collected value with the help of this feature.

The map and timeline can also be used to navigate a chart that represents the collected data over a period of time. User(s) can define the time period in which to have data presented by using an adjustment mechanism such as sliding handles. For example, a user may manipulate an on-screen cursor via a keyboard, touch screen and/or mousing device to move one or more sliding bars or handles to define a time period of interest. Alternatively and/or in addition, parameters entered via keyboard, touch screen, etc., may be used to specify a time period or window for display, output, and/or further processing, for example.

In addition, specific values and data can be flagged at important points in time to denote changes in a patient's health, for example. In certain embodiments, the flagged values may appear in a secondary area, for example, to give maximum viewing area to the flowsheet itself. By clicking on any of the flagged values, for example, a user may be taken to that "time-period" in the flowsheet.

In certain embodiments, a date slider is positioned above the flowsheet. The date slider displays milestone dates in a patient's medical history via letters, numbers and/or other indicators, for example. In certain embodiments, a list of the flagged dates may be provided with the flowsheet to allow a care provider to click on a date and have that date's data presented.

Thus, certain embodiments can help provide a faster and more efficient care provider workflow for flowsheet navigation. Certain embodiments can help increase productivity in patient data review. Certain embodiments incorporate a visual, time-based navigation system such as a map and timeline with a flowsheet presentation of patient data. Certain embodiments provide an ability to view data over expanded timelines (e.g., days/months/years) in a flowsheet.

As shown, for example, in FIG. 1, certain embodiments provide a flowsheet 100 used in accordance with an embodiment of the present invention. The flowsheet 100 includes patient data 110, a timeline 120, and milestone area 130, for example.

The patient data 110 represents medical history data for one or more patients found in the flowsheet 100. In certain embodiments, the data may be aggregated from one or more sources, for example.

The timeline 120 illustrates a period of time over which data has been collected for one or more patients in the flowsheet 100. The timeline 120 includes one or more navigator icons 140, such as bars, sliders, handles, icons, and/or the like, to allow a user to move along the timeline 120. An example of another slider 180 is also illustrated in FIG. 1. In certain embodiments, as illustrated in window 145, navigator icons 140 may be used to restrict the timeline 120 to a certain period or window of time, for example. The timeline 120 may include one or more dates 160 and/or date intervals indicating periods of time along the timeline 120, for example.

In certain embodiments, the timeline 120 also includes a graphical representation 170 which can be used to represent an aggregate amount of data or events for a patient during a period of time. The graphical representation 170 may alternatively and/or in addition visually indicate a value for a certain type of collected data, as well as visually indicate a variation or trend in that value (e.g., through a line graph over time), for example.

The timeline 120 also includes one or more indicators 150, such as letters, numbers, icons, etc., indicating milestone and/or other date(s) of interest in the timeline 120. For example, indicators 150 may include the letters A-I, as shown in FIG. 1, indicating certain milestone dates for events in the patient's medical history. Indicators 150 correspond to items or entries in the milestone area 130. When a user selects an indicator 150 in the timeline 120, an entry 135 in the milestone area 130 is accessed. In certain embodiments, information for one or more event(s) on a particular date may be accessed through selection of either the indicator 150 and/or the milestone entry 135. In certain embodiments, the milestone entry 135 provides additional description not provided by the indicator 150 to better allow a user to select data point(s) of interest, for example.

As an example, illustrated in FIG. 1, a user may view the flowsheet 100 including data 110 for a patient. The timeline 120 indicates several events 150 as letters A-I in the medical history for the patient. The milestone area 130 enumerates events A-I as admissions, tests, diagnoses, procedures, etc. for the patient. The user selects an event indicator 150 to access more detailed information about that event. For example, the user can see that the patient had a heart attack on May 15, 2002, as represented by indicator A. A user may select the indicator A in the timeline 120 to access further information regarding the patient's heart attack. Information may be displayed with patient data 110, for example.

In certain embodiments, information for a particular event may be connected with information for related events and/or decision support resources, for example. The related information and/or resources may be accessible via the flowsheet 100 and/or a companion application running on a healthcare system workstation, for example.

Certain embodiments provide methods and systems providing comprehensive clinical documentation for a patient's entire lifetime in one easy-to-use interface. Certain embodiments enable a patient's entire medical history to be displayed, edited and interacted within one context. Users may view an entire gestalt of a patient history or timeline at a high level to better understand an overall health of a patient. From a high level overall vantage point, the user may navigate to any specific item on the patient's history by using a navigational cursor, mouse click, touch screen, voice command, gaze tracking, etc. The user can drill down to isolated metadata in the timeline to view specific lab reports, physical exam notes, procedures, etc. Thus, a user can navigate a complete set of patient healthcare data via a unified interface by scrolling, dragging, expanding, shrinking, etc., via the interface.

A patient EMR and/or other record may be represented in a flowsheet and may include a medical history for a patient as well as data with time stamps (or times and dates at which data was collected or entered). Types of data may include test names, test results, imaging procedures, medical visits (e.g., hospital, office, clinic, etc.), medical problem, caregiver encounter, medical procedure, symptoms, biological analysis, finding, medication, acquisition, etc. These types/categories of data can each be represented by a symbol on a common and/or individual timeline for each event of the data occurrence, for example.

In certain embodiments, EMR flowsheets can present data in visual manner by presenting a timeline with symbols or other indicators representing each patient encounter. A patient encounter can include any test, visit, or other encounter with any physician, nurse, radiologist, image technician or other caregiver, for example. With many patient encounters, the timeline can get too cluttered and difficult to visualize associations between data. Data can be associated in a number of ways, such as by patient encounter (e.g., office/hospital visit/stay), time/date range, problem (e.g., diabetes, heart disease, broken bone, etc.), procedure (e.g., surgery, series of lab tests, etc.), collecting/entering hospital/clinic/caregiver, etc.

In certain embodiments, a rendering engine may "chart" or map aggregated data into a single timeline interface. As new data is collected, the rendering engine can "redraw" the timeline and update the interface.

In certain embodiments, comprehensive patient data points may be aggregated into a single location (e.g., a thumbdrive, CD, DVD, hard drive, etc.). Export capability from a plurality of clinical applications allows aggregation and storage of information to a single locale.

A user may navigate, manipulate and view different information and different levels/granularity of information in the flowsheet 100 by dragging, scrolling and/or otherwise moving within the timeline 120 via mouse and cursor, keyboard, trackball, touch screen, voice command, etc. Based on particular events or problems, the user may choose to retrieve greater detail. In certain embodiments, information displayed may have hyperlinks attached to allow the user to navigate to an information system that initially generated the data to drill down on finer details. Alternatively and/or in addition, finer details related to the information may be present in a patient history context and become viewable and reviewable as the user drills down into the timeline 120.

In certain embodiments, a flowsheet 100 can aggregate information from a plurality of information systems under a common patient context. Information systems may include a radiology information system (RIS), a picture archiving and communication system (PACS), Computer Physician Order Entry (CPOE), an electronic medical record (EMR), Clinical Information System (CIS), Cardiovascular Information System (CVIS), Library Information System (LIS), and/or other healthcare information system (HIS), for example. An interface facilitating access to the patient record may include a context manager, such as a clinical context object workgroup (CCOW) context manager and/or other rules-based context manager. Components may communicate via wired and/or wireless connections on one or more processing units, such as computers, medical systems, storage devices, custom processors, and/or other processing units. Components may be implemented separately and/or integrated in various forms in hardware, software and/or firmware, for example.

Certain embodiments may be used to provide an integrated solution for application execution and/or information retrieval based on rules and context sharing, for example. For example, context sharing allows information and/or configuration options/settings, for example, to be shared between system environments. Rules, for example, may be defined dynamically and/or loaded from a library to filter and/or process information generated from an information system and/or an application.

Information for a particular patient may be extracted and/or linked from one or more information systems for presentation to a user via a unified patient record timeline 120, for example. In certain embodiments, information retrieval, display and/or processing settings, for example, may be customized according to a particular user or type of user. Retrieval, aggregation, display and/or processing of information may be based on rules, preferences, and/or other settings, for example. Rules, preferences, settings, etc. may be generated automatically based on preset parameters and/or observed data, for example. Rules, preferences, settings, etc., may be created by a system administrator or other user, for example. Rules, preferences, settings, etc., also may be manually and/or automatically adapted based on experiences, for example.

In certain embodiments, a user may log on any one of the connected systems and/or a separate system to access information found on all of the connected systems through context sharing and a unified user interface. In certain embodiments, information may be filtered for easier, more effective viewing.

In certain embodiments, a user interface providing a flowsheet and timeline for a patient record may work together with a perspectives management system for handling multiple applications and workflow, for example. The perspectives management system allows various perspectives to be defined which save workflow steps and other information for a particular user. Perspectives may be used to save visual component positioning information and interactions based on workflow, for example. Perspectives allow relevant information to be presented to a user.

In certain embodiments, a flowsheet provides patient data including identification information, allergy and/or ailment information, history information, orders, medications, progress notes, flowsheets, labs, images, monitors, summary, administrative information, and/or other information, for example. The flowsheet may include a list of tasks for a healthcare practitioner and/or the patient, for example. The flowsheet may also identify a care provider and/or a location of the patient, for example.

In certain embodiments, an indication may be given of, for example, normal results, abnormal results, and/or critical results. For example, the indication may be graphical, such as an icon. The user may select the indicator to obtain more information. For example, the user may click on an icon to see details as to why a result was abnormal. The user may be able to view only certain types of results. For example, the user may view only critical results.

Filters and/or rules may be provided for views and/or categories. Ranges, such as values or dates, may be specified for data. Default views, categories, filters, rules, and/or ranges may be provided. In certain embodiments, default values may be modified by a user and/or based on operating conditions. In certain embodiments, new views, categories, filters, rules, ranges, etc., may be created by a user.

For example, a filter may be used to filter medical results data presented to a user according to one or more variables. For example, when a filter is selected by a user, a modification routine applies the filter to the results displayed to the user in the current view by removing from display all medical results that do not fall within the filter. As described above, a variable may be any data or information included in medical data. For example, a variable may include one or more of a type (or item) and/or range of laboratory test results, vital sign measurements, fluids administered to a patient, and/or fluids measured from a patient. A variable may include text from notes, laboratory reports, examination reports, one or more captions to a laboratory test result, vital sign measurement, and/or fluids administered to/measured from a patient, an order for a laboratory test, treatment and/or prescription, and/or a name.

By specifying one or more limits on one or more variables, a user may create a filter to be applied to results presented in a results window.

Figure 2:
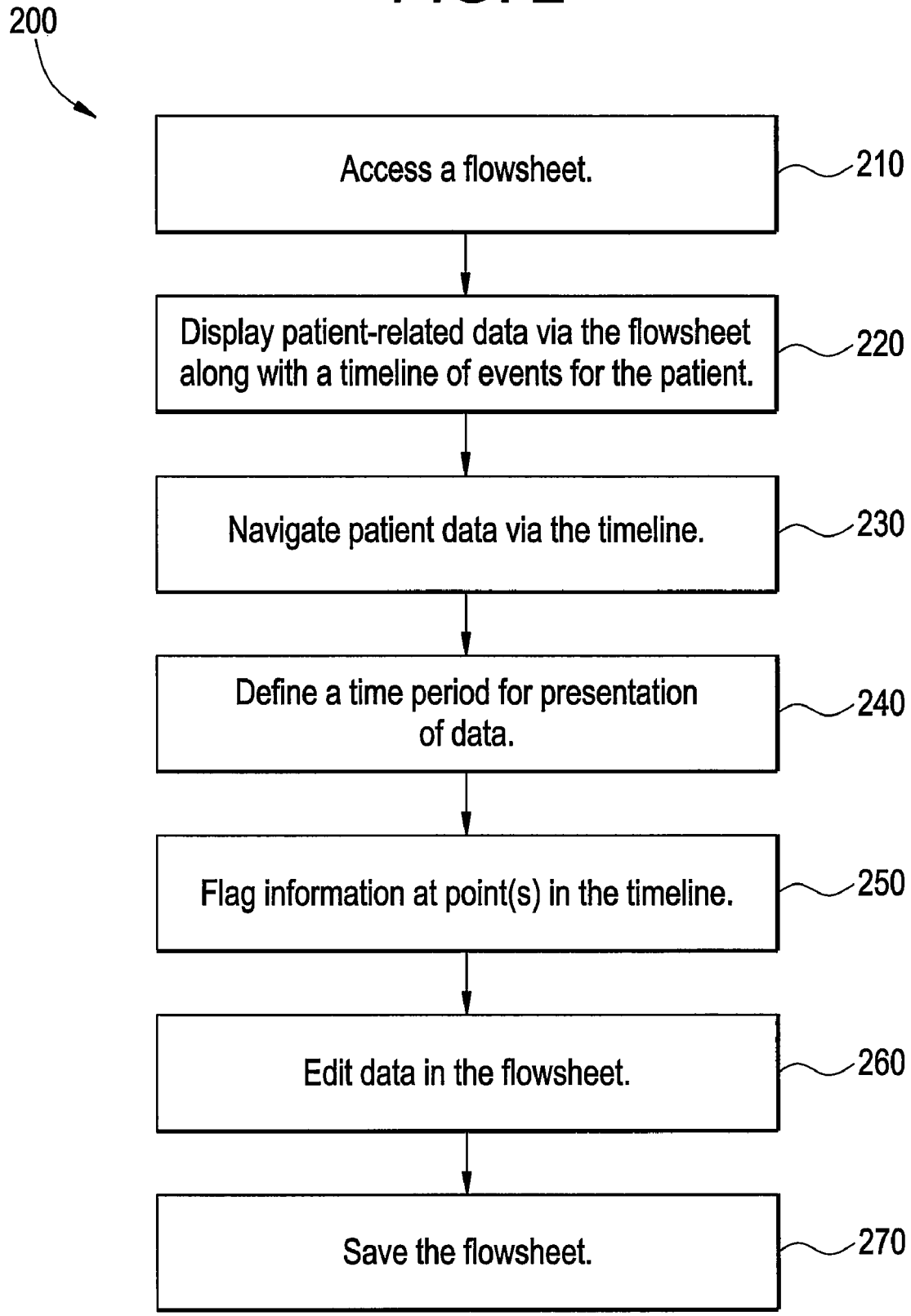
FIG. 2 illustrates a flow diagram for a method for navigating through a large longitudinal data set using a miniature representation of the dataset in a flowsheet according to an embodiment of the present invention.
Figure 3:
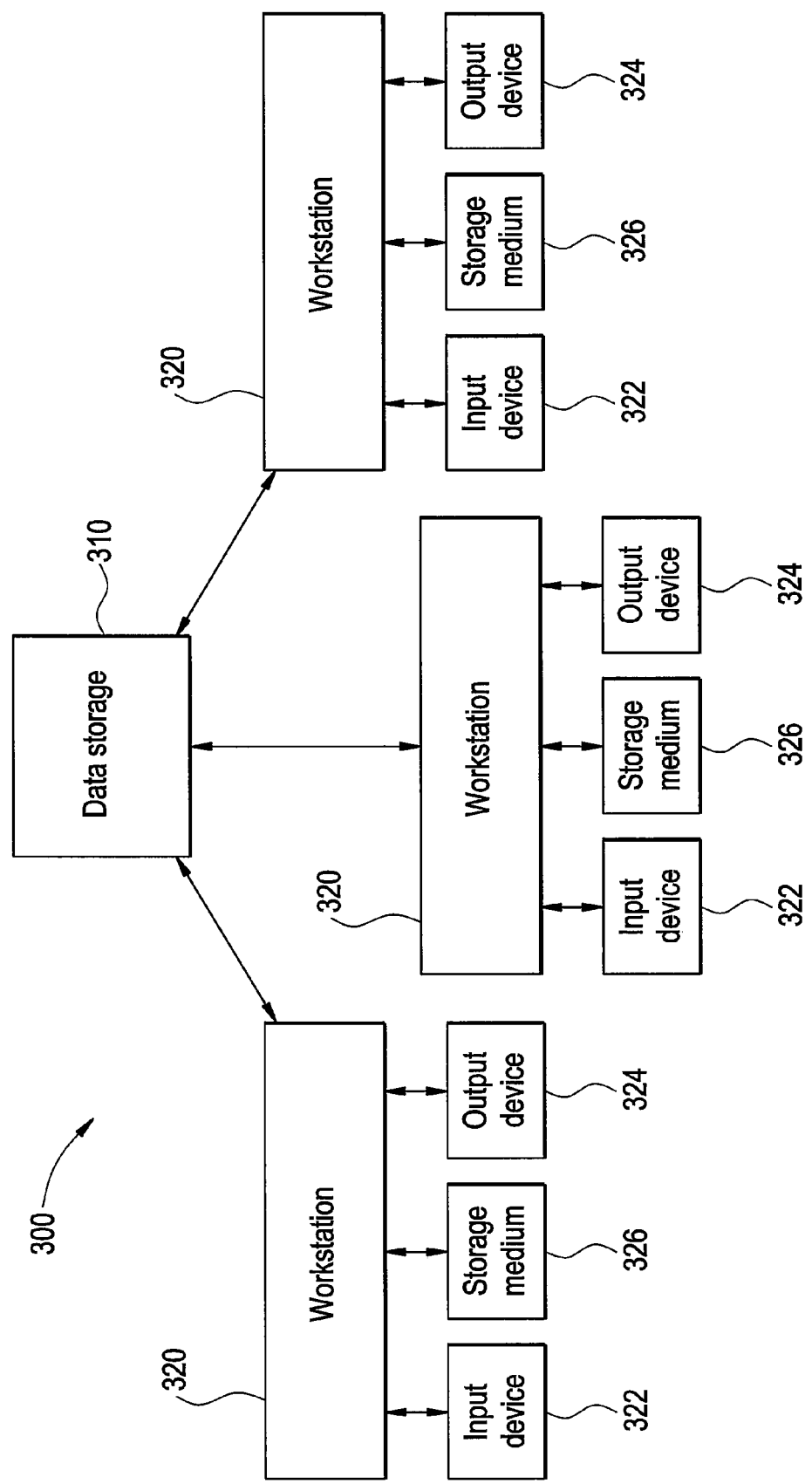
FIG. 3 illustrates a system for clinical data storage and retrieval in accordance with an embodiment of the present invention.

FIG. 2 illustrates a flow diagram for a method 200 for navigating through a large longitudinal data set using a miniature representation of the dataset in a flowsheet according to an embodiment of the present invention. At step 210, a flowsheet is accessed. For example, a flowsheet for a particular patient is opened on a healthcare information system workstation. As described above, the flowsheet may include patient data, flagged values, a timeline, and one or more mechanisms to view and/or manipulate the data.

In certain embodiments, as described above, flowsheet data may be aggregated from a plurality of sources for the patient such as from one or more information systems, imaging systems, laboratory systems, and/or other sources. For example, data for the identified or otherwise selected patient is retrieved from one or more sources, such as a PACS, RIS, EMR, HIS, etc., and aggregated or combined into a timeline or comprehensive view of patient data over the life of the patient. Data may be saved and/or presented in a certain patient context or perspective, for example.

At step 220, patient-related data is displayed via the flowsheet along with a timeline of events for the patient. As described above, the flowsheet may include a timeline and a dataset represented as a miniature map of information with respect to the timeline.

At step 230, patient data is navigated via the timeline. For example, users may navigate the map using the timeline to display collected at a particular point and/or period of time. In certain embodiments, data may be navigated and viewed via the graphical map and/or via a patient chart including alphanumeric patient data, for example.

At step 240, a time period can be defined for presentation of data. For example, a user may manipulate buttons, sliding handles, arrow keys, etc., to define a time period within the timeline during which data is presented to the user.

At step 250, information can be flagged at points in time in the timeline. For example, specific values and data can be flagged at important points in time in the history of the patient to denote changes in patient health and/or other events. In certain embodiments, flagged values may appear in a secondary area of the display apart from the flowsheet and chart. In certain embodiments, clicking on or otherwise selecting a flagged value takes you to that time period in the flowsheet, for example.

At step 260, a user may edit data in the flowsheet. For example, a user may annotate data points in the flowsheet. As another example, a user may open and edit one or more data points included in the flowsheet using one or more input sources such as a keyboard, touch screen, stylus, voice command, eye tracking, etc. A user may add and/or delete one or more data points in the flowsheet, for example. A user may tag or bookmark one or more data points for easier notice/access in later use, for example.

At step 270, a user may save the flowsheet. The patient record may be saved to an information system, EMR, portable medium, smart card, barcode, etc. Thus, modifications/annotations to the flowsheet may be saved for later retrieval and/or other use.

One or more of the steps of the method 200 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

In certain embodiments, a timeline may be viewed and/or constructed using a system such as system 300 including at least one data storage 310 and at least one workstation 320. While three workstations 320 are illustrated in system 300, a larger or smaller number of workstations 320 can be used in accordance with embodiments of the presently described technology. In addition, while one data storage 310 is illustrated in system 300, system 300 can include more than one data storage 310. For example, each of a plurality of entities (such as remote data storage facilities, hospitals or clinics) can each include one or more data stores 310 in communication with one or more workstations 320.

As illustrated in system 300, one or more workstations 320 can be in communication with at least one other workstation 320 and/or at least one data storage 310. Workstations 320 can be located in a single physical location or in a plurality of locations. Workstations 320 can be connected to and communicate via one or more networks.

Workstations 320 can be directly attached to one or more data stores 310 and/or communicate with data storage 310 via one or more networks. Each workstation 320 can be implemented using a specialized or general-purpose computer executing a computer program for carrying out the processes described herein. Workstations 320 can be personal computers or host attached terminals, for example. If workstations 320 are personal computers, the processing described herein can be shared by one or more data stores 310 and a workstation 320 by providing an applet to workstation 320, for example.

Workstations 320 include an input device 322, an output device 324 and a storage medium 326. For example, workstations 320 can include a mouse, stylus, microphone and/or keyboard as an input device. Workstations 320 can include a computer monitor, liquid crystal display ("LCD") screen, printer and/or speaker as an output device.

Storage medium 326 of workstations 320 is a computer-readable memory. For example, storage medium 326 can include a computer hard drive, a compact disc ("CD") drive, a USB thumb drive, or any other type of memory capable of storing one or more computer software applications. Storage medium 326 can be included in workstations 320 or physically remote from workstations 320. For example, storage medium 326 can be accessible by workstations 320 through a wired or wireless network connection.

Storage medium 326 includes a set of instructions for a computer (described in more detail below). The set of instructions includes one or more routines capable of being run or performed by workstations 320. The set of instructions can be embodied in one or more software applications or in computer code.

Data storage 310 can be implemented using a variety of devices for storing electronic information such as a file transfer protocol ("FTP") server, for example. Data storage 310 includes electronic data. For example, data storage 310 can store EMRs for a plurality of patients.

Communication between workstations 320, workstations 320 and data storage 310, and/or a plurality of data stores 310 can be via any one or more types of known networks including a local area network ("LAN"), a wide area network ("WAN"), an intranet, or a global network (for example, Internet). Any two of workstations 320 and data stores 310 can be coupled to one another through multiple networks (for example, intranet and Internet) so that not all components of system 300 are required to be coupled to one another through the same network.

Any workstations 320 and/or data stores 310 can be connected to a network or one another in a wired or wireless fashion. In an example embodiment, workstations 320 and data store 310 communicate via the Internet and each workstation 320 executes a user interface application to directly connect to data store 310. In another embodiment, workstation 320 can execute a web browser to contact data store 310. Alternatively, workstation 320 can be implemented using a device programmed primarily for accessing data store 310.

Data storage 310 can be implemented using a server operating in response to a computer program stored in a storage medium accessible by the server. Data storage 310 can operate as a network server (often referred to as a web server) to communicate with workstations 320. Data storage 310 can handle sending and receiving information to and from workstations 320 and can perform associated tasks. Data storage 310 can also include a firewall to prevent unauthorized access and enforce any limitations on authorized access. For instance, an administrator can have access to the entire system and have authority to modify portions of system 300 and a staff member can only have access to view a subset of the data stored at data store 310. In an example embodiment, the administrator has the ability to add new users, delete users and edit user privileges. The firewall can be implemented using conventional hardware and/or software.

Data store 310 can also operate as an application server. Data store 310 can execute one or more application programs to provide access to the data repository located on data store 310. Processing can be shared by data store 310 and workstations 320 by providing an application (for example, a java applet). Alternatively, data store 310 can include a standalone software application for performing a portion of the processing described herein. It is to be understood that separate servers may be used to implement the network server functions and the application server functions. Alternatively, the network server, firewall and the application server can be implemented by a single server executing computer programs to perform the requisite functions.

The storage device located at data storage 310 can be implemented using a variety of devices for storing electronic information such as an FTP server. It is understood that the storage device can be implemented using memory contained in data store 310 or it may be a separate physical device. The storage device can include a variety of information including a data warehouse containing data such as patient medical data, for example.

Data storage 310 can also operate as a database server and coordinate access to application data including data stored on the storage device. Data storage 310 can be physically stored as a single database with access restricted based on user characteristics or it can be physically stored in a variety of databases.

In an embodiment, data storage 310 is configured to store data that is recorded with or associated with a time and/or date stamp. For example, a data entry can be stored in data storage 310 along with a time and/or date at which the data was entered or recorded initially or at data storage 310. The time/date information can be recorded along with the data as, for example, metadata. Alternatively, the time/date information can be recorded in the data in manner similar to the remainder of the data. In another alternative, the time/date information can be stored in a relational database or table and associated with the data via the database or table.

In an embodiment, data storage 310 is configured to store medical data for a patient in a flowsheet and/or patient chart. The medical data can include data such as numbers and text. The medical data can also include information describing medical events. For example, the medical data/events can include a name of a medical test performed on a patient. The medical data/events can also include the result(s) of a medical test performed on a patient. For example, the actual numerical result of a medical test can be stored as a result of a medical test. In another example, the result of a medical test can include a finding or analysis by a caregiver that entered as text.

In another example, the medical data/events can include the name and/or results of an imaging procedure. Such imaging procedures include, but are not limited to, CT scans, MRI scans, photographs, tomographic images, and computer models, for example.

The medical data/events can also include a description of a medical visit. For example, the medical data/event can list the date and/or time of a visit to a hospital, doctor's office or clinic, as well as details about what tests, procedures or examinations were performed during the visit. In addition, the data/event can include results of the tests, procedures and examinations as described above. The data/event can include the names of all caregivers that came into contact or provided medical care to the patient during the visit. The data/event can also include information on the length of the visit, as well as any symptoms complained of by a patient and/or noted by a caregiver or other staff.

In another example, the medical data/events can include a description of a medical problem that a patient is experiencing. For example, an injury can be recorded as a medical problem, as well as any illnesses (chronic or otherwise) a patient is experiencing.

The medical data/events can also include details of a caregiver encounter. For example, the data/event can include information such as the date/time of an encounter with a doctor, nurse or other caregiver (such as a radiologist, for example). The data/event can include additional information such as what medical tests, examinations or procedures were performed on a patient by a specific caregiver. For example, if nurse "X" takes a blood sample from a patient, records the weight of a patient and tests the patient's blood pressure, then all of these tests and procedures, as well as the results, can be recorded as medical data/events associated with nurse X.

In another example, medical data/events can include a description and/or results of a medical procedure. For example, the name and outcome of a surgery or outpatient procedure can be recorded as a medical procedure.

Medical data/events can also include a description of any symptoms experienced by a patient. This information can be recorded as text or by a codification scheme. For example, medical data/events can include descriptions such as a headache, chest pains or dizziness.

The medical data/events stored in a patient flowsheet can also include any biological analyses performed on the patient. For example, the data/events can include the numerical results of blood, enzyme or other fluid tests. In another example, the data/events can include a text description of the results of a biological analysis.

In another example, the medical data/events can include a finding by a caregiver. A finding can include any numeric and/or text-based description of a discovery or analysis made by the caregiver. For example, a radiologist can analyze a series of x-ray images of a patient and find a growth or tumor in the patient. The radiologist can then record his or her finding in a patient flowsheet or record.

The medical data/events can also include one or more medications a patient is or has taken. The data can include the date, time, dosage and/or name of medication, for example.

The medical data/events can also include one or more acquisitions. An acquisition can include any actual data acquired and/or the date at which the data is acquired. For example, an acquisition can include the results and/or date/time at which results from a laboratory test were acquired.

One or more types of similar data/events is included in a category of data/events. In continuing with the above example, a category of medical data/events can include all "tests" (including all test results or "test results" being a separate category), "imaging procedures" (including all images obtained therefrom or "images" being a separate category), "visit," "problems," "encounters," "medical procedures" (including all results or "medical procedure results" being a separate category), "symptoms," "biological analyses" (including all results of such analyses or "biological analysis result(s)" being a separate category), "findings," "medications," and/or "results."

While the above provides several examples of the types of medical data/events that can be used in accordance with embodiments of the presently described technology, it is to be understood that the presently described technology is not limited to the above data/events. In addition, while some types of information stored as medical data/events described above is repeated, it is to be understood that various medical data/events can be stored multiple times. For example, if a patient complains of a symptom to a caregiver during a particular office visit, the symptom can be recorded by itself and/or with additional information, such as the name of the caregiver and any procedures performed on the patient.

In an embodiment, the medical data/events include the actual information desired to be stored. Alternatively, the medical data/events can include a code representative of the actual information desired to be stored. For example, the codes provided by the International Statistical Classification of Diseases and Related Health Problems ("ICD") can be stored in place of the actual information related to the medical data/event.

In operation, a user employs a workstation 320 to display, on an output device 324, a flowsheet including a timeline of data and/or events stored at data storage 310 in a chronological order with data graphically and alphanumerically represented to the user. As described above, workstation 320 includes computer-readable storage medium 326 that itself comprises a set of instructions for workstation 320. The set of instructions can be embodied in one or more computer software applications or computer code. This set of instructions is used by workstation 320 to access and display data and/or events and provide the data/events in a flowsheet including a data map with timeline, patient chart, and secondary flagged area for emphasis of certain identified events/data, for example. Thus, at least one technical effect of the set of instructions is to allow presentation, navigation and manipulation of a large patient data set in a flowsheet using a map and timeline arrangement.

The set of instructions includes one or more software routines. In an embodiment of the presently described technology, the set of instructions includes a user interface routine displaying data for a patient via a flowsheet along with a timeline of events relating to the patient, wherein the data is represented in alphanumeric and graphical map form. The user interface routine facilitates navigation of the patient data using the timeline and allows a user to flag events in the patient data along the timeline. The set of instructions also includes a processing routine defining a time period for presentation of patient data along the timeline in the flowsheet.

In certain embodiments, the processing routine and user interface routine provide information regarding flagged events in a secondary area of the flowsheet. In certain embodiments, the user interface routine allows a user to select a flagged event to access a corresponding point along the timeline and view data for the flagged event at the point in time. In certain embodiments, the processing routine aggregates data from a plurality of healthcare information sources for display and access via the flowsheet and the user interface routine. In certain embodiments, the processing routine facilitates editing and saving of patient data by a user. In certain embodiments, the flowsheet includes a patient healthcare data set represented as a map including a timeline as an axis for the map, wherein the map is navigated to display data collected at a certain part of the timeline.

Data/events can be displayed by representing each of the data/events by a symbol on one or more timelines, for example. Timelines may include medical events belonging to particular categories, for example. These timelines are also referred to as timeline metaphors. Timeline metaphors can be used in EMR software applications to provide users with the ability to navigate through a patient's medical history chronologically. In many cases, every patient encounter with a caregiver or hospital is listed as a separate item on a timeline. For example, timelines may present medical events and/or data by illustrating the date and/or time at which the medical event or data occurred, was collected or was entered.

In an embodiment, each data/event is represented by a graphical symbol. The exact symbol used can differ in accordance with the presently described technology. In an embodiment, the same symbol is used for all similar data/events. For example, the same symbol can be used for all medical data/events in a category of data/events.

A timeline can include data/events from a given category presented in chronological order. The number of timelines therefore can change based on the number of categories of data/events to be presented.

In certain embodiments, a user can select which categories and/or timelines are displayed. For example, using input device 322, the user can select one or more categories to be presented on output device 324. The display routine and the data routine can then obtain the data/events in the selected category(ies) and display the data/events as shown in a presentation on output device 324. In addition, the user can select the date and/or time range over which the data/events are to be presented in timelines.

In an embodiment, a user can scroll an icon over a symbol and the display routine will cause additional information related to the symbol to be presented to the user. For example, a user can employ input device 322 to move an arrow displayed on output device 324 over a symbol. Once the arrow is over the symbol (or once the user "clicks" or otherwise selects the symbol using input device 322), additional information about the data/event represented by symbol can be presented by the display routine on output device 326. For example, the display routine can cause popup window to appear and present the actual data/event (or a portion thereof) represented by the symbol.

In certain embodiments, a filter may be created by a user. The filter is used to determine which symbols represent events/data that are associated with one another, if any.

The filter comprises one or more rules. These rules are compared to all or a subset of the events/data. If any of the events/data satisfy or match each of the rules, the events/data are considered to be associated with one another. Such events/ data are referred to as associated events/data. If any of the events/data do not satisfy or match all of the rules, the events/ data are considered to not be associated with one another.

In an embodiment, a user creates a filter by employing input device 322 to select one or more predefined rules that are displayed on output device 326. The selected rules are then included in the filter.

In another embodiment, a user employs input device 322 to select a predefined filter. The predefined filter is a filter previously created by a user and stored on a computer-readable memory such as data store 310 or storage medium 326, for example.

The rules can include any criteria useful to determine whether a given data/event or subset of data/events fall within, or satisfy, the rule. For example, a rule can be stated as all data/events collected and/or entered during a particular patient's visit to a hospital. All data/events that were collected and/or entered during that visit would therefore fall within the scope of this rule and therefore be considered associated data/events.

In another example, a rule can define a set of data/events that are normally related with one another. For example, a typical doctor's office visit for a physical involves several routine tests such as tests on blood pressure, weight, reflexes, and/or blood. A rule can set one or more criteria that would include all medical data/events in a patient's record that include information about and the results for blood pressure tests, weight measurements, reflex test results and blood test results. This rule can then be applied to a patient chart to determine which medical data/events includes data from blood pressure tests, weight measurements, reflex test results and blood test results. This data is then considered to be associated data.

In another example, a rule can define one or more criteria that associate all data/events related to a single patient encounter or a selected time and/or date range. Such a criteria can state that all data/events that were collected and/or entered during that encounter or during the time and/or date range selected by the user.

Another example of a rule is one in which all data/events from a particular medical test or examination are associated with one another. For example, a rule can state that all data/ events describing a test and the results of that test are associated. Such a rule would associate a description of a blood test and all chemical and biological analyses from that blood test as associated data/events.

In another example, a rule can define one or more criteria that associate all data/events collected and/or entered by one caregiver or group of caregivers and excludes all data/events collected and/or entered by all other caregivers. For example, such a rule can associate all test results collected by a particular nurse and exclude all test results entered by other nurses.

In another example, a rule can define one or more criteria that associate all data/events with a predefined association with a selected medical problem and/or medical procedure. For example, the data/events stored at data store 310 can have a predefined association with one another based on an underlying problem or test. The medical problem of diabetes could have predefined association with tests such as eye examinations, foot examinations, blood sugar test results, hemoglobin A1c results and urine tests, for example. A medical procedure such as a surgery can have a predefined association with one or more caregivers' names involved in the surgery and in the recovery from surgery, test results related to the surgery and/ or related symptoms, for example. All data/events with such predefined associations can be considered associated data/ events according to such a rule.

The predefined associations can be stored or recorded in a variety of manners. For example, metadata included in the actual data/events stored at data store 310 can include the predefined associations. In another example, the actual data/ events can have the predefined associations recorded in the data itself. A relational database or table stored at data store 310 can also include the predefined associations, for example.

Once the filter is selected or created by a user, the filter is used to determine if any associations exist among the data/ events displayed on output device 326. A filter routine can determine if any associations exist among the displayed data/ events by applying the filter to the data/events. The filter routine can apply the filter by comparing the criteria defined by the rule(s) of the filter to the data/events displayed on output device 326. For example, the filter routine can apply the filter by searching through all or a subset of data/events stored at data store 310 and comparing the criteria of the filter rule(s) to the data/events.

In certain embodiments, a rendering engine may "chart" or map aggregated data into a single timeline data map, such as the timeline and data map described above. As new data is collected, the rendering engine can "redraw" the timeline and update the data map and flowsheet.

The components, elements, and/or functionality of the interface(s) and system(s) described above may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device, such as, for example, a PACS workstation or one or more dedicated processors.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system.

As noted above, certain embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Certain embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Certain embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any healthcare information system utilizing flowsheets. Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A healthcare information system providing a clinical flowsheet for data review, said system comprising:
a processor coupled to a memory, wherein the processor is programmed to implement:
a clinical flowsheet including:
a patient healthcare data set represented as a map of patient data including a timeline as an axis for the map, wherein the map is navigable to display, within said flowsheet, data collected at a certain part of the timeline;
a patient chart of data from the patient healthcare data set collected over a period of time, the patient chart navigable in relation to the map within the flowsheet; and
a secondary area in the flowsheet including flagged data values labeled in the timeline and found in the patient chart; and
an interface to access said flowsheet,
wherein the map, the patient chart, and the secondary area are to be displayed as part of the flowsheet and are interrelated to display data from the patient healthcare data set in the flowsheet in response to a user selection in any of the map, the patient chart, and the secondary area, and
wherein the interface allows data to be flagged in the map along the timeline, wherein flagged data values appear in a secondary area of the flowsheet, and wherein the interface allows a user to select a flagged data value to access a corresponding point along the timeline and view data for at least one event at the point in time, wherein data displayed in the map, the patient chart, and the secondary area is updated in response to selection of an event in any of the map, the patient chart, and the secondary area.

2. The system of claim 1, wherein the timeline allows a user to define a time period for data to be viewed in the flowsheet map.

3. The system of claim 1, further comprising at least one control for scaling the timeline to view a particular period of time.

4. The system of claim 1, wherein the system aggregates data from a plurality of healthcare information sources for display and access via the flowsheet.

5. A computer-implemented method for navigating a patient healthcare data set using a representation of the dataset in a flowsheet, said method comprising:
displaying, using a processor, data for a patient via a flowsheet, the data represented in alphanumeric as well as graphical map form, the flowsheet including a patient healthcare data set represented as a map of patient data including a timeline as an axis for the map, wherein the map is navigable to display, within said flowsheet, data collected at a certain part of the timeline; a patient chart of data from the patient healthcare data set collected over a period of time, the patient chart navigable in relation to the map within the flowsheet; and a secondary area in the flowsheet including flagged data values labeled in the timeline and found in the patient chart, wherein the map, the patient chart, and the secondary area are to be displayed as part of the flowsheet and are interrelated to display data from the patient healthcare data set in the flowsheet in response to a user selection in any of the map, the patient chart, and the secondary area;

navigating, using the processor, the patient data using any one of the timeline and the secondary area;

allowing, using the processor, a user to flag events in the patient data along the timeline, wherein information regarding flagged events appears in the secondary area of the flowsheet;

defining a time period for presentation of patient data along the timeline in the flowsheet; and allowing a user to select a flagged event to access a corresponding point along the timeline and view, using the processor, data for the flagged event at the point in time, wherein data displayed in the map, the patient chart, and the secondary area is updated in response to selection of an event in any of the map, the patient chart, and the secondary area.

6. The method of claim 5, further comprising aggregating data from a plurality of healthcare information sources for display and access via the flowsheet.

7. The method of claim 5, further comprising saving the patient data after editing by a user.

8. A non-transitory computer readable medium having a set of instructions for execution on a computer, said set of instructions comprising:

a user interface routine to display data for a patient via a flowsheet, the data being represented in alphanumeric and graphical map form, the flowsheet including a patient healthcare data set represented as a map of patient data including a timeline as an axis for the map, wherein the map is navigable to display, within said flowsheet, data collected at a certain part of the timeline; a patient chart of data from the patient healthcare data set collected over a period of time, the patient chart navigable in relation to the map within the flowsheet; and a secondary area in the flowsheet including flagged data values labeled in the timeline and found in the patient chart, wherein the map, the patient chart, and the secondary area are to be displayed as part of the flowsheet and are interrelated to display data from the patient healthcare data set in the flowsheet in response to a user selection in any of the map, the patient chart, and the secondary area, the user interface routine to facilitate navigation of the patient data using any one of the timeline and the secondary area and to allow a user to flag events in the patient data along the timeline; and a processing routine defining a time period for presentation of patient data along the timeline in the flowsheet, wherein the processing routine and user interface routine provide information regarding flagged events in a secondary area of the flowsheet and wherein the user interface routine allows a user to select a flagged event to access a corresponding point along the timeline and view data for the flagged event at the point in time, wherein data displayed in the map, the patient chart, and the secondary area is updated in response to selection of an event in any of the map, the patient chart, and the secondary area.

9. The computer readable medium of claim 8, wherein the processing routine aggregates data from a plurality of healthcare information sources for display and access via the flowsheet and the user interface routine.

10. The computer readable medium of claim 8, wherein the processing routine facilitates editing and saving of patient data by a user.

* * * * *